(12) United States Patent
Reyes et al.

(10) Patent No.: US 8,796,187 B2
(45) Date of Patent: Aug. 5, 2014

(54) ADDITIVES TO SUPPRESS SILICA SCALE BUILD-UP

(75) Inventors: Enrique A. Reyes, Duncan, OK (US);
Jimmie D. Weaver, Duncan, OK (US);
Matt E. Blauch, Duncan, OK (US);
Corine L. McMechan, Duncan, OK (US)

(73) Assignee: Halliburton Energy Services, Inc., Houston, TX (US)

( * ) Notice: Subject to any disclaimer, the term of this patent is extended or adjusted under 35 U.S.C. 154(b) by 33 days.

(21) Appl. No.: 13/422,953

(22) Filed: Mar. 16, 2012

(65) Prior Publication Data
US 2012/0172263 A1 Jul. 5, 2012

Related U.S. Application Data

(62) Division of application No. 12/574,037, filed on Oct. 6, 2009.

(51) Int. Cl.
| | | |
|---|---|---|
| C09K 8/64 | (2006.01) | |
| C09K 8/60 | (2006.01) | |
| C09K 8/588 | (2006.01) | |
| C09K 8/528 | (2006.01) | |
| C09K 8/54 | (2006.01) | |
| C09K 8/68 | (2006.01) | |

(52) U.S. Cl.
CPC .............. C09J 8/805 (2013.01); *Y10S 507/901* (2013.01)
USPC ........... 507/233; 507/205; 507/219; 507/221; 507/224; 507/225; 507/223; 507/269; 507/273; 507/901

(58) Field of Classification Search
CPC ....... C09K 8/52; C09K 8/528; Y10S 507/924
USPC ......... 507/233, 901, 205, 219, 221, 222, 224, 507/225, 269, 271, 273
See application file for complete search history.

(56) References Cited

U.S. PATENT DOCUMENTS

| | | |
|---|---|---|
| 3,704,750 A | 12/1972 | Miles et al. |
| 3,782,469 A | 1/1974 | Fulford |
| 3,826,311 A | 7/1974 | Szabo et al. |
| 4,323,124 A | 4/1982 | Swan |
| 4,427,068 A | 1/1984 | Fitzgibbon |
| 4,454,914 A | 6/1984 | Watanabe |
| 4,460,627 A | 7/1984 | Weaver et al. |
| 4,585,064 A | 4/1986 | Graham et al. |
| 4,606,227 A | 8/1986 | Walters |
| 4,741,400 A | 5/1988 | Underdown |
| 5,159,979 A * | 11/1992 | Jennings, Jr. ............... 166/308.2 |
| 5,277,823 A | 1/1994 | Hann et al. |
| 5,529,125 A | 6/1996 | Di Lullo Arias et al. |
| 6,613,899 B1 | 9/2003 | Kuzee et al. |
| 7,232,793 B1 | 6/2007 | King et al. |
| 2003/0091467 A1 | 5/2003 | Kmec et al. |
| 2004/0023818 A1* | 2/2004 | Nguyen et al. ................. 507/209 |
| 2004/0074643 A1 | 4/2004 | Munoz et al. |
| 2005/0194135 A1 | 9/2005 | Nguyen et al. |
| 2005/0244641 A1* | 11/2005 | Vincent .......................... 428/403 |
| 2006/0065396 A1 | 3/2006 | Dawson et al. |
| 2006/0102345 A1* | 5/2006 | McCarthy et al. .......... 166/250.1 |
| 2006/0260808 A1 | 11/2006 | Weaver et al. |
| 2006/0272816 A1* | 12/2006 | Willberg et al. ............... 166/279 |
| 2007/0079965 A1 | 4/2007 | Nguyen et al. |
| 2008/0011477 A1* | 1/2008 | Rediger et al. ............. 166/280.2 |
| 2008/0135245 A1 | 6/2008 | Smith et al. |
| 2009/0233819 A1 | 9/2009 | Fuller et al. |
| 2010/0089578 A1 | 4/2010 | Nguyen et al. |
| 2010/0089579 A1 | 4/2010 | Reyes et al. |
| 2010/0093566 A1 | 4/2010 | Reyes et al. |

FOREIGN PATENT DOCUMENTS

| | | |
|---|---|---|
| CA | 2 198 812 | 8/1998 |
| CA | 2 509 115 A1 | 12/2005 |
| CA | 2 545 563 A1 | 11/2006 |
| CA | 2 685 832 A1 | 11/2008 |
| EP | 0082657 A2 | 6/1983 |
| EP | 0459661 A1 | 12/1991 |
| GB | 2298440 A | 9/1996 |
| WO | WO2005100007 A2 | 10/2005 |
| WO | 2010041032 A1 | 4/2010 |

OTHER PUBLICATIONS

Official Action for Canadian Patent Application No. 2,738,978 dated May 29, 2012.
Official Action for Australian Patent Application No. 2009300847 dated Apr. 12, 2012.
Kalfayan, Leonard, "Production Enhancement with Acid Stimulation," PennWell Corporation, 2000.
Kalfayan, Leonard, "Production Enhancement with Acid Stimulation," 2nd ed., PennWell Corporation, 2008.
SPE 130641 Weaver et al., "Productivity Impact from Geochemical Degradation of Hydraulic Fractures," Society of Petroleum Engineers, 2010.
SPE 150669 Raysoni et al., "Long-Term Proppant Performance," Society of Petroleum Engineers, 2012.
SPE 118175 Nguyen et al., "Prevention of Geochemical Scaling in Hydraulically Created Fractures: Laboratory and Field Studies," Society of Petroleum Engineers, 2008.

(Continued)

*Primary Examiner* — Aiqun Li
(74) *Attorney, Agent, or Firm* — McDermott Will & Emery LLP; Craig W. Roddy

(57) ABSTRACT

Composition comprising a plurality of particulates wherein at least some particulates are at least partially covered with a coating that impedes the intrusion of water into the particulates; and, a silica scale control additive, wherein the silica scale control additive is capable of suppressing silica scale build-up proximate the plurality of particulates. Some compositions further include a treatment fluid wherein and the silica scale control additive are present in the treatment fluid.

6 Claims, No Drawings

(56) References Cited

OTHER PUBLICATIONS

International Search Report and Written Opinion for PCTGB2011/001547, not dated.

Official Action for Australian Patent Application 2009300846 dated Feb. 13, 2014.
Official Action for EP Application 09 737 117.3 dated Jan. 31, 2014.

* cited by examiner

ADDITIVES TO SUPPRESS SILICA SCALE BUILD-UP

CROSS-REFERENCE TO RELATED APPLICATIONS

This application claims benefit of U.S. Provisional Patent Application Ser. Nos. 61/104,610, 61/104,620, 61/104,624, and 61/104,629, each filed Oct. 10, 2008.

This application is related to U.S. patent application Ser. No. 12/573,999 (U.S. Patent Application Publication 2010/0089578), entitled "Prevention of Water Intrusion into Particulates," by Nguyen et al., U.S. patent application Ser. No. 12/574,018 (U.S. Patent Application Publication 2010/0093566), entitled "Ceramic Coated Particulates," by Reyes et al., and U.S. patent application Ser. No. 12/574,054 (U.S. Patent Application Publication 2011/0253374), entitled "Geochemical Control of Fracturing Fluids," by Reyes et al., filed on Oct. 6, 2009, which are hereby incorporated by reference in their entirety.

BACKGROUND

The present disclosure relates to treatments and compounds useful in subterranean formations, and, at least in some embodiments, to treatments and compounds wherein particulates and/or surfaces may be subject to silica scale build-up.

In the production of fluids, such as hydrocarbons or water, from a subterranean formation, the subterranean formation should be sufficiently conductive to permit the flow of desirable fluids to a well bore penetrating the formation. Among others, hydraulic fracturing may be a useful treatment for increasing the conductivity of a subterranean formation. Hydraulic fracturing operations generally may involve pumping a treatment fluid (e.g., a fracturing fluid or a "pad fluid") into a well bore that penetrates a subterranean formation at a sufficient hydraulic pressure to create or enhance one or more pathways, or "fractures," in the subterranean formation. Enhancing a fracture generally involves extending or enlarging a natural or pre-existing fracture in the formation. These fractures generally increase the permeability of that portion of the formation. The treatment fluid may comprise particulates, including proppant particulates that are deposited in the resultant fractures. The particulates are thought to help prevent the fractures from fully closing upon release of the hydraulic pressure, forming conductive channels through which fluid may flow between the formation and the well bore.

It is generally believed that the surfaces of particulates generally comprise minerals, which may react with other substances (e.g., water, minerals, treatment fluids, and the like) that reside in the subterranean formation in chemical reactions caused, at least in part, by conditions created by mechanical stresses on those minerals (e.g., fracturing of the mineral surfaces or the compaction of particulates). These reactions are herein referred to as "stress-activated reactions" or "stress-activated reactivity." One type of these stress-activated reactions may be diageneous reactions. As used herein, the terms "diageneous reactions," "diageneous reactivity," and "diagenesis" include chemical and/or physical processes that, in the presence of water, move a portion of the mineral in a particulate and/or convert a portion of the mineral in a particulate into some other form. A mineral that has been so moved or converted is herein referred to as a "diageneous product" or "diagenic product." Any particulate comprising a mineral may be susceptible to these diageneous reactions, including natural silicate minerals (e.g., quartz), man-made silicates and glass materials, metal oxide minerals (both natural and man-made), and the like.

Two of the principal mechanisms that diagenesis reactions are thought to involve are "pressure dissolution" and "precipitation processes." Where two water-wetted mineral surfaces are in contact with each other at a point under strain, the localized mineral solubility near that point may increase, causing the minerals to dissolve. Minerals in solution may diffuse through the water film outside of the region where the mineral surfaces are in contact (e.g., the pore spaces of a particulate pack), where they may precipitate out of solution. The dissolution and precipitation of minerals in the course of these reactions may reduce the conductivity of a particulate pack, inter alia, by clogging the pore spaces in the particulate pack with mineral precipitate and/or collapsing the pore spaces by dissolving solid mineral in the "walls" of those pore spaces. In other instances, minerals on the surface of a particulate may exhibit a tendency to react with substances in the reservoir, formation, and/or treatment fluids that are in contact with the particulates, such as water, gelling agents (e.g., polysaccharides, biopolymers, etc.), and other substances commonly found in these fluids. Molecules from such substances may become anchored to the mineral surface of the particulate. These types of reactivity may further decrease the conductivity of a subterranean formation, inter alia, through the obstruction of conductive fractures in the formation by any molecules that have become anchored to the particulates resident within those fractures. Both types of reactions may generally require the presence of a fluid, such as water, to occur to any significant extent.

Silica (silicon dioxide) appears naturally in a number of crystalline and amorphous forms, all of which are sparingly soluble in water; thus leading to the formation of undesirable deposits. Silicates can be salts derived from silica or the silicic acids, especially orthosilicates and metasilicates, which may combine to form polysilicates. Silica solubility depends on, but not exclusively, a number of factors such as pH, temperature, and ionic composition. Most silicates, except the alkali silicates, are sparingly soluble in water. A number of different forms of silica and silicate salt deposits are possible, and formation of deposits depends, among other factors, on the temperature and pH of the water.

SUMMARY

The present disclosure relates to treatments and compounds useful in subterranean formations, and, at least in some embodiments, to treatments and compounds wherein particulates and/or surfaces may be subject to silica scale build-up.

One embodiment of the present invention provides a method. The method comprises providing a silica scale control additive in a subterranean formation. The method further comprises providing a particulate pack in the subterranean formation. The method further comprises allowing the silica scale control additive to suppress silica scale build-up proximate the particulate pack.

Another embodiment of the invention provides another method. The method comprises providing a fluid comprising a carrier fluid, a plurality of particulates, and a silica scale control additive. The method further comprises introducing the fluid into a subterranean formation. The method further comprises allowing at least some of the particulates to form a particulate pack in the subterranean formation. The method further comprises allowing the silica scale control additive to suppress silica scale build-up proximate the particulate pack.

Yet another embodiment of the invention provides a composition. The composition comprises a plurality of particulates a silica scale control additive, wherein the silica scale control additive is capable of suppressing silica scale build-up proximate the particulate pack.

The features and advantages of the present invention will be apparent to those skilled in the art. While numerous changes may be made by those skilled in the art, such changes are within the spirit of the invention.

DESCRIPTION OF PREFERRED EMBODIMENTS

The present disclosure relates to treatments and compounds useful in subterranean formations, and, at least in some embodiments, to treatments and compounds wherein particulates and/or surfaces may be subject to silica scale build-up.

The term "coating" as used herein refers to at least a partial coating of some or all of the particulates. Neither complete nor substantial coverage of the particulates or mix of particulates is implied by the term "coating." Rather, a particulate may be coated if it has, for example, at least a partial coating.

The term "derivative" is defined herein to include any compound that is made from one of the listed compounds, for example, by replacing one atom in the listed compound with another atom or group of atoms, rearranging two or more atoms in the listed compound, ionizing one of the listed compounds, or creating a salt of one of the listed compounds. A derivative of a material may include, but is not limited to, a compound composition based on a plurality of base materials, a composite material, or an aggregated material of various compositions.

As used herein, the terms "diageneous reactions," "diageneous reactivity," and "diagenesis" include chemical and physical processes that, in the presence of water, move a mineral and/or convert a mineral into some other form. Examples of such minerals include, but are not limited to, oxides or hydroxides of zirconium, magnesium, aluminum, titanium, calcium, strontium, barium, radium, zinc, cadmium, boron, gallium, iron, or any other element suitable for forming a diagenic product. Such minerals may be found in a particulate, in a formation, and/or introduced into a formation as "diagenesis source material." A mineral that has been so moved or converted is herein referred to as a "diageneous product" or "diagenic product."

As used herein, the term "aqueous fluid interaction" includes a variety of possible interactions between an aqueous fluid and a particulate. Such interactions may include infiltration of the aqueous fluid into the particulate, for example, by infiltrating pores, voids, crevices, cracks, and/or channels at or near the surface of the particulate. Such interactions may also include diagenesis.

As used herein, the term "diffusion barrier" includes any sort of material, including a coating, on or proximate to a particle that impedes and/or prevents aqueous fluid interaction with the particle. For example, some diffusion barriers fill or coat pores, voids, crevices, cracks, or channels at or near the particle's surface to impede and/or prevent infiltration by the aqueous fluid. As another example, some diffusion barriers impede and/or prevent diagensis.

As used herein, the term "diagenic protective materials" refers to one or more diagenic products that may be selectively promoted in order to form a diffusion barrier.

As used herein, the term "filler" or "filler material" means a particulate material that is capable of fitting within a pore, void, crevice, crack, or channel at or near the surface of a particulate or on surfaces within the porous matrix of the individual particulates.

As used herein, the term "relatively low molecular weight" refers to a molecular weight that would encompass monomers and short-chain polymers having physical dimensions from a few angstroms to several hundred nanometers.

As used herein, a "monolayer" refers to a coating of a material approximately one unit thick. For chemicals, this may mean a coating as thin as one molecule, and for particulate compositions, it may mean a coating one particulate grain deep.

As used herein, the terms "pores," "voids," "crevices," "cracks," and "channels" refer to features at or near the surface of a particulate. Any given particulate may have one or more pores, voids, crevices, cracks, or channels, or may be free of such features. One or more such features may be generally referred to as "surface features." The use of the terms in conjunction is in no way intended to indicate that all three must be present simultaneously, or at all, in order for the teachings of the present disclosure to apply.

As used herein, the terms "particle," "particulate," "proppant particulate," and "gravel" are all used to refer to either a single particle or a plurality of particles which may be used for supporting a fracture in an underground formation, for forming a proppant pack, or for use in forming a gravel pack. Such particles may be disposed in a subterranean formation, including in spaces in the rock itself, fractures within the rock, and/or a well bore penetrating the subterranean formation.

As used herein, the term "pack" or "particulate pack" refers to a collection of particulates within an enclosed volume, wherein the particulates may be juxtaposed and/or in contact with one another, and wherein pore spaces may be disposed between the particulates. Examples of "packs" may include "proppant packs," which may refer to a collection of proppant particulates within a fracture, and/or "gravel packs," which may refer to a grouping of particulates that are packed sufficiently close together so as to prevent the passage of certain materials through the pack.

The term "on-the-fly" is used herein to indicate that one flowing stream comprising particulates is introduced into another flowing stream comprising a hydrophobic coating agent so that the streams are combined and mixed to flow as a single stream. In some instances, the streams may be combined to flow as a single stream as part of an on-going treatment at the job site. Such mixing can also be described as "real-time" mixing.

As used herein, the term "silica scale control additive" may be any product capable of suppressing silica scale build-up by increasing the solubility of silica in solution, inhibiting silica polymer chain propagation, and/or decreasing the size or quantity of any silica scale created in a solution.

The term "gel," as used herein and its derivatives refer to a viscoelastic or semi-solid, jelly-like state assumed by some colloidal dispersions.

If there is any conflict in the usages of a word or term in this specification and one or more patent or other documents that may be incorporated herein by reference, the definitions that are consistent with this specification should be adopted for the purposes of understanding this invention.

There are many advantages of the present invention, only some of which are mentioned here. One advantage of the methods disclosed herein may be the suppression of silica scale build-up within a particulate pack in a subterranean formation, including in the rock itself, fractures within the rock, and/or a well bore penetrating the subterranean formation. Without limiting the invention to a particular theory or mechanism, it is nonetheless currently believed that, when placed within a formation, a particulate pack may experience silica scale build-up due to silicon dissolution from either the particulates or the formation. The silicon may dissolve in fluids, such as formation fluids or treatment fluids. The dissolved silicon may then precipitate in various forms to create silica scale within, upstream, or downstream of the particulate pack. Such silica scale may have a tendency to form or collect in the interstitial spaces of the particulate pack, which may reduce the permeability of the pack over time. As such, the suppression or inhibition of silicon dissolution and silica scale build-up may be able to reduce the permeability loss in the particulate pack, thereby increasing the ultimate productivity of the well.

Protecting particulates from such damage may be achieved in several ways. In an embodiment, a silica scale control additive may be utilized to treat a particulate pack. The silica scale control additive may suppress silica scale build-up by increasing the solubility of silicon within the particulate pack while simultaneously preventing large build-ups of silica scale. Various silica scale control additives may be used to limit the silica scale formation, as discussed in more detail below.

Protecting particulates from damaging interactions with aqueous fluids may be achieved in several ways. In accordance with embodiments of the present invention, these generally may include treating a particulate with a diffusion barrier which acts to impede the particulate interaction with aqueous fluids during and/or after placement in the formation. The diffusion barrier may comprise one of several types of materials, including hydrophobic materials, diagenic protective materials, and various polymeric compositions. Some embodiments of the present invention may utilize filler material to fill the pores, voids, crevices, cracks, or channels that may be present in a particulate surface. Alternatively, a filler material may be used to generate and/or place the diffusion barrier. For example, a hydrophobic material may be used to coat a filler material, and the filler material may then generate a diffusion barrier (e.g., comprising a diageneous product) on the particulates. The filler material may fill the pores, voids, crevices, cracks, or channels on the particulate surface, resulting in a surface that may be more hydrophobic than the original particulate surface. Each of these materials and methods will be described in more detail below.

The particulates that may be used in embodiments of the present invention include any proppant or gravel particulates that may be used in a subterranean application. Suitable particulates may include sand, sintered bauxite, silica alumina, glass beads, etc. Other suitable particulates include, but are not limited to, sand, bauxite, garnets, fumed silica, ceramic materials, glass materials, polymer materials, polytetrafluoroethylene materials, nut shell pieces, seed shell pieces, fruit pit pieces, wood, composite particulates, proppant particulates, degradable particulates, coated particulates, gravel, and combinations thereof. Suitable composite materials may comprise a binder and a particulate material wherein suitable particulate materials may include silica, alumina, garnets, fumed carbon, carbon black, graphite, mica, titanium dioxide, meta-silicate, calcium silicate, kaolin, talc, zirconia, boron, fly ash, hollow glass microspheres, solid glass, and combinations thereof. In certain embodiments, the particles may comprise common sand. In some embodiments, a derivative of one or more of the particulate materials may also be used. Derivatives may include materials such as compounds, composite materials, and aggregated materials of various compositions. In some embodiments of the present invention, some or all of the particulates may be comprised of a diagenesis source material. In this embodiment, the particulates may comprise oxides or hydroxides of zirconium, magnesium, aluminum, titanium, calcium, strontium, barium, radium, zinc, cadmium, boron, gallium, iron, or any other element suitable for forming a diagenic product. Suitable particulates may take any shape including, but not limited to, the physical shape of platelets, shavings, flakes, ribbons, rods, strips, spheres, spheroids, ellipsoids, toroids, pellets, or tablets. Although a variety of particulate sizes may be useful in the present invention, in certain embodiments, particulate sizes may range from about 200 mesh to about 8 mesh.

Embodiments of particulates of the present invention may contain pores, voids, crevices, cracks, or channels at or near the surface. For example, SEM micrographs at high magnification may show that the surfaces of particles, such as particulates made from bauxite, may be laden with pores, voids, crevices, cracks, and channels. Without being limited by theory, it is believed that these pores, voids, crevices, cracks, or channels at or near the particulate surface may provide a direct path to allow a detrimental interaction between aqueous fluids and the particles that may lead to degradation of the particles under formation pressure and temperature.

In some embodiments, the particulates may be treated or coated with one or more suitable substances. Generally, the particulates may be treated or coated with any substance which is suitable for traditional particulate treatments. In certain embodiments, the particulates may be coated so as to impede the intrusion of water into the particulates. For example, the particulates may be coated and/or used as discussed in "Prevention of Water Intrusion Into Particulates" by Nguyen et al., U.S. patent application Ser. No. 12/573,999 (U.S. Patent Application Publication 20100089578); "Geochemical Control of Fracturing Fluids" by Reyes et al., U.S. patent application Ser. No. 12/574,054 (U.S. Patent Application Publication 20110253374); and/or "Ceramic Coated Particulates" by Reyes et al., U.S. patent application Ser. No. 12/574,018 (U.S. Patent Application Publication 20100093566), each filed on the same day herewith, and the entire disclosures of which are hereby incorporated by reference in their entirety. In an embodiment, a portion of the particulates may be coated so as to limit their diagenic reactivity while others may remain uncoated so as to provide a reaction site for the diagenesis source material.

The particle compositions used in some of the embodiments of the present invention may comprise at least one particulate and a diffusion barrier, which may comprise a hydrophobic, or water repellant, material. Diffusion barriers may be initiated by and/or formed from a variety of materials. For example, certain materials may initiate diffusion barriers in some embodiments of the present invention. Suitable materials may be any chemical agent capable of forming a hydrophobic coating on the surface of particulates. In certain embodiments, particles comprising a diffusion barrier may have a retained strength greater than or equal to about 30%, as discussed in more detail below. In some embodiments, such diffusion barriers may enhance the recovery of a reservoir, formation, and/or treatment fluid. In certain embodiments, a surfactant may be included in the coating material so as to improve the coating process. Suitable coating materials may include oligomeric materials, monomeric materials, oil-wetting compounds, and combinations thereof to provide at least a monomolecular film, which may make the mineral surfaces water-repellent or hydrophobic.

In one embodiment, a diffusion barrier may comprise the reaction products of a compound having a reactive silyl group. The diffusion barrier may be formed by forming a silicon oxide layer or hybrid organo-silicon oxide anchor layer from a humidified reaction product of silicon tetrachloride or trichloromethysilane, followed by the vapor-deposition of a chloroalkylsilane. In another embodiment, the diffusion barrier may comprise a trimethylsilyl functional group. For example, if a fumed silica filler particle is used, the surface hydroxyl groups may be replaced with trimethylsilyl functional groups to form a hydrophobic filler particle. The diffusion barrier may also comprise silicones or siloxanes. In an embodiment, the diffusion barrier may comprise an organosilicon compound, which may include, for example, an organosiloxane, an organosilane, a fluoro-organosiloxane, and a fluoro-organosilane. The diffusion barrier may also comprise a polysiloxane or an organo-modified polysiloxane, which may include a di-betaine polysiloxane or a di-quaternary polysiloxane.

In another embodiment, a diffusion barrier may comprise polymers of a fluoroalkyl-group containing silane compound, and the polymers may include at least dimers and trimers of the silane compound. This diffusion barrier may be made by preparing a solution, the solution being produced by subjecting a fluoroalkyl-group contained silane compound to a hydrolysis and a condensation polymerization to produce at least dimers and trimers of the silane compound, coating the solution onto the surface of the particulate or filler material, and heating the material to cause the fluoroalkyl group in the solution to be bonded to the surface of the particulate solids so as to form a hydrophobic film on the material. In another embodiment, the diffusion barrier may comprise a fluoro-organosiloxane or a fluoro-organosilane compound, which may include, for example, 2-(n-perfluoro-octyl)-ethyltriethoxysilane and perfluoro-octyldimethyl chlorosilane.

In yet another embodiment, a diffusion barrier may comprise a polyamide. In still another embodiment, the diffusion barrier may comprise a silyl-modified polyamide.

In an embodiment, a diffusion barrier may comprise polytetrafluoroethylene, plant oils, hydrocarbons, copolymerized polyvinylidene chloride, or any other substance capable of hindering or preventing aqueous fluid penetration, permeation, or wetting of a particulate.

In an embodiment, the particulates may be coated with a ceramic. The ceramic may impede aqueous fluid interactions between the particulates and aqueous fluids, including aqueous treatment and/or formation fluids. In an embodiment, an appropriate ceramic may include silicon carbide, silicon nitride, boron carbon, boron carbide, diamond-like-carbon, titanium carbide, aluminum nitride, chromium carbide, mixed carbide, nitride, carbonitride alloys, and cubic boron nitride. In an embodiment, a plurality of ceramics may be used in conjunction to combine advantageous effects. In an embodiment, a derivative of one or more ceramic materials may also be used. Derivatives may include materials such as compounds, composite materials, and aggregated compositions of various ceramic materials.

One of ordinary skill in the art, with the benefit of this disclosure, will be able to determine which ceramic or ceramics should be coated on a particulate based on, for example, formation chemistry, formation conditions (e.g., temperature, pressure, etc.), particulate composition, resource availability, costs and logistics considerations, and any physical limitations inherent in the coating process. In an embodiment, the coating layer may vary in thickness depending on the subterranean operation requirements. In some embodiments, the ceramic may be a monolayer thick, while in other embodiments, a thicker layer may be desired. In particular, some embodiments may provide a very thin ceramic layer of subatomic thickness. In such embodiments, the ceramic thickness may be between about 100 nanometers and about 50,000 nanometers. The resulting coated particulate may have ceramic from between about 0.1% to about 10% by weight of the particulate. In another embodiment providing a ceramic layer of subatomic thickness, the ceramic thickness may be between about 100 nanometers and about 500 nanometers. The resulting coated particulate may have ceramic from between about 0.5% to about 2% by weight of the particulate.

In some embodiments, a variety of methods may be useful in coating a ceramic on particulates. Any method capable of coating a ceramic on a particulate may be used. In an embodiment, chemical vapor deposition, physical vapor deposition, dip coating, spray pyrolysis, sputtering, sintering, and chemical vapor infiltration may be used to introduce ceramic onto a particulate. For any methods requiring a chemical reaction to form a ceramic coating (e.g., chemical vapor deposition or spray pyrolysis), any appropriate precursors may be determined by one skilled in the arts. For example, single source precursors for forming silicon carbides may include, but are not limited to, polycarbosilanes, polysilazanes, silylenes, perfluoroalkylsilanes or functionalized silylenes, and mixtures such as alkylchlorosilanes, ethylene, and hydrogen for instance. One skilled in the art will be able to determine the appropriate coating technique, reaction conditions, and precursors, if needed, based upon the type of ceramic desired and the particulate composition. For embodiments in which more than one layer of the ceramic is coated on the particulates, the same or different coating methods may be used. Due to the conditions generally required to form a ceramic coating on a particulate, the particulates may generally be coated in a manufacturing process prior to being shipped to the well site. In some embodiments, the particulates may be coated at the well site and/or on-the-fly.

Certain methods of the present invention may result in a very thin diffusion barrier, comprising a protective material, a diagenic product, a treated filler material, or any combination thereof on a particulate. The use of relatively low molecular weight compounds in the coating methods may result in diffusion barriers as thin as a monolayer. In another embodiment, filler materials may act to produce a diffusion barrier on a particulate less than about 10 micrometers thick. In an alternative embodiment, the diffusion barrier may be less than about 1 micrometer thick, or alternatively less than about 0.5 micrometers thick. Such thin coatings may effectively allow the coating of the pores, voids, crevices, cracks, or channels of the particulates. This may help to limit the particulate degradation due to interactions with aqueous fluids while preventing any detrimental interactions between the particulates due to agglomeration of the particulate pack.

In another embodiment of the present invention, a method of initiating a fluid barrier may comprise coating a filler particle with a protective coating, such as a hydrophobic material, and then mixing the coated filler particle with a particulate to form a diffusion barrier. For example, a fumed silica nano-particle may be treated such that surface hydroxyl groups are replaced with trimethylsilyl functional groups to form a protective coating on the filler material. In this example, the particulates may exhibit hydrophobic properties when mixed with the coated filler material. For another example, the filler material may be a metallic compound capable of promoting the formation of diagenic products when placed in the formation. In this example, the particulates may be coated with filler material, and a diffusion barrier may be formed upon placement in the formation. In an embodiment, the filler material may be a dry, free-flowing material suitable for mixing with a particulate. The treated filler material may be mixed with the particulates in an amount sufficient to impart a diffusion barrier to the particulates. This may be an amount sufficient to partially coat the particulates but not provide 100% coverage of each particle. In an embodiment, the treated filler material may be mixed with the particulates in an amount ranging from about 0.025% to 50% by weight of particulates, or from about 0.25% to 50% by weight of particulates. In an alternative embodiment, the treated filler material may be mixed with the particulates in an amount ranging from about 0.25% to 5% by weight of particulates.

The filler material may comprise materials with particles of micrometer-size, sub-micrometer-size, nano-size, or a combination thereof. The filler material may be reinforcing or non-reinforcing. Filler materials may include, for example, fumed silica, fused silica, garnet powder, clay, mica, alumina, finely divided quartz powder, amorphous silicas, meta-silicates, calcium silicates, calcine, kaoline, talc, zirconia, fly ash, boron, carbon black, fumed carbon, graphite, diamond, silicone carbide, aluminum hydrates, metal nitrides (such as boron nitride, and aluminum nitrides), metal oxides (such as aluminum oxide, zinc oxide, titanium dioxide or iron oxide), and any combination thereof. In another embodiment, the filler material may comprise metal particles, such as aluminum, zirconium, titanium, or derivatives thereof. In one embodiment, the average diameter of the filler material particles may be less than about 20 micrometers. In one embodiment, the average filler material particle diameter may range from about 0.05 micrometers to about 10 micrometers, or from about 0.1 micrometers to about 10 micrometers. In another embodiment, the particles of filler material may have a size range of from about 0.1 micrometer to about 0.5 micrometers, or from about 0.2 micrometers to about 0.5 micrometers.

In accordance with embodiments of the present invention, the filler material particle size may be chosen, among other purposes, to achieve a coating of a particulate including the pore spaces on the particulate surface. The choice of a filler material particle size may be based upon a consideration of the surface characteristics of the particulate, which may be based on the choice of particulate material, crystal structure, and/or other characteristics. In an embodiment, the filler material particle size may be such that the maximum filler material particle size may be at least equal to, and, in some embodiments, less than, the expected diameter of a pore, void, crevice, crack, or channel at or near the surface of the particulate. Consideration of any additional coating thickness that the coating material may add to the filler material also may be a consideration in choosing a filler material having certain particle sizes and shapes.

In an embodiment, a silica scale control additive may be used with a particulate pack (e.g., a proppant or gravel pack) to suppress silica scale build-up by mitigating, inhibiting, or suppressing the formation and build-up of silica (also known as silica scale). Formation of silica scale may occur on the particulates, on the formation fracture face, or in a solution within a particulate pack. Silica scale control additives may increase the amount of soluble silica within a solution. Without intending to be limited by theory, it is believed that the silica scale control additives inhibit the polymerization and build-up of silicic acid and colloidal silica by disrupting chain propagation. In an embodiment, a silica scale control additive may be any compound which controls the formation of scale to some degree and does not negatively react with the particulates, the formation, a treatment fluid, a formation fluid, or any other aspect of the subterranean environment. In an embodiment, suitable silica scale control additives may include polyaminoamide dendrimers and polyethyleneimine, which may be combined with carboxymethylinulin and polyacrylates. In an alternative embodiment, polyallylamines, copolymers of polyacrylamides, and polyallyldiamethylammonium chloride may also be used as silica scale control additives. Examples of suitable silica scale control additives include ACUMER™ 5000 (a proprietary polymer having a molecular weight of 5000 that is commercially available from Rohm and Hass of Philadelphia, Pa.); CLA-STA® XP (a water-soluble cationic oligomer of trimethylamine-quaternized polyepichlorohydrin that preferentially adsorbs and replaces gel from clay and silica surfaces) and CLA-STA® FS (a polymer that stabilizes mineral fine particles by adsorbing on formation surfaces), each of which is available from Halliburton Energy Services, Inc. of Duncan, Okla.

In some embodiments, a silica scale control additive may be added to a treatment fluid (e.g., a fracturing fluid, a carrier fluid, a stimulation fluid, etc.) in an amount sufficient to suppress silica scale build-up by inhibiting the formation of silica scale. The treatment fluid may be aqueous, non-aqueous, or a combination of fluid types. Generally, the treatment fluid may comprise a carrier fluid, particulates, such as proppant, and one or more additives, such as silica scale control additives. In some embodiments, the amount of silica scale control additive may be any amount necessary to control silica and silicate deposition in the system being treated. In an embodiment, the amount may be any amount sufficient to obtain a retained permeability in a proppant pack of at least about 40%, the measurement of which is described in more detail below. In an embodiment, the amount of silica scale control additive may range from about 1 to about 1000 parts per million (ppm) by weight of the carrier fluid. In an alternative embodiment, the amount may range from about 1 to about 100 ppm by weight of the carrier fluid. The pH of the carrier fluid may also have an impact on the effectiveness of the silica scale control additive. In some embodiment, the pH of the carrier fluid may be maintained at between about 4.0 and about 8.0. In an embodiment, the pH of the carrier fluid may be maintained between about 6.5 and about 7.5.

Silica scale control additives may be added to a well bore before, after, or during the placement of a particulate pack. In an embodiment, the silica scale control additive may be added to a fracturing fluid and carried with the fracturing fluid during formation of the fractures. In this embodiment, the silica scale control additive may be in the fracturing fluid in the formation during the placement and setting of a particulate pack. Alternatively, the silica scale control additive may be mixed with a carrier fluid used to carry and set the particulate pack in the formation. In still another embodiment, a silica scale control additive may be utilized after a particulate pack has been placed in the well bore. In such embodiments, a carrier fluid may be used to carry the silica scale control additive into the well bore and through the particulate pack. By way of example, a particulate pack may be contacted by a silica scale control additive. This technique also may be used as a subsequent treatment method to periodically treat the particulate pack over time, among other purposes, in order to maintain permeability in the particulate pack.

One embodiment of the present invention provides a method. The method comprises providing a silica scale control additive in a subterranean formation. The method further comprises providing a particulate pack in the subterranean formation. The method further comprises allowing the silica scale control additive to suppress silica scale build-up proximate the particulate pack. In some embodiments, this method may be useful in the recovery of fluids from the subterranean formation. The fluids being recovered may be a fluid previously introduced into the subterranean formation, an aqueous reservoir and/or formation fluid, a hydrocarbon fluid, or a combination thereof.

Another embodiment of the invention provides another method. The method comprises providing a fluid comprising a carrier fluid, a plurality of particulates, and a silica scale control additive. The method further comprises introducing the fluid into a subterranean formation. The method further comprises allowing at least some of the particulates to form a particulate pack in the subterranean formation. The method further comprises allowing the silica scale control additive to suppress silica scale build-up proximate the particulate pack. In some embodiments, this method may be useful in the recovery of fluids from the subterranean formation. The fluids being recovered may be a fluid previously introduced into the subterranean formation, an aqueous reservoir and/or formation fluid, a hydrocarbon fluid, or a combination thereof.

Yet another embodiment of the invention provides a composition. The composition comprises a plurality of particulates a silica scale control additive, wherein the silica scale control additive is capable of suppressing silica scale build-up proximate the particulate pack. In some embodiments, this method may be useful in preparation of particulates for subterranean treatments and/or usage of particulates in subterranean treatments.

In order to quantify the mechanical strength of the particulates and permeability of the particulate pack, both before and after exposure to formation conditions and fluids, several test procedures may be utilized to determine various particulate properties. The first test method studies temperature-promoted diagenesis of a particulate pack by exposing a particulate pack to a flowing solution of simulated formation fluid at an approximate formation temperature. The second procedure studies stress/temperature-promoted diagenic growth through exposure of a particulate pack to a static flow environment under simulated formation pressures and temperatures. The mechanical strength of individual particulates may be measured before and after the test procedures to determine the percentage of particulate strength lost due to exposure to formation temperature or pressure. Alternatively, the permeability of the particulate pack may be measured before and after the temperature-promoted diagenesis test in order to determine a retained permeability value for the particulate pack. As would be understood by one of ordinary skill in the art with the benefit of this disclosure, expected subterranean formation conditions (e.g., temperature, pressure, formation fluid composition) for a selected subterranean formation will determine the appropriate formation conditions for test procedures.

In the temperature-promoted diagenesis test procedure, deionized water may first be heated to a test temperature of between about 200 degrees Fahrenheit (° F.) and about 600° F. by passing it through a heat exchanger coil. Simulated formation fluid may be formed by passing the deionized water through multiple packs of crushed formation material arranged in series. The number of formation packs required for the test may vary such that the simulated formation fluid leaving the last pack may be in equilibrium with the crushed formation material. Through experimentation, the typical number of formation packs may generally be between about 1 and about 10. Crushed formation material may be screened to remove fines and an approximately $8/35$ mesh fraction may be used in the formation packs.

In an embodiment, once a simulated formation fluid in equilibrium with the crushed formation material is obtained, the simulated formation fluid may be directed to a column containing a particulate pack. The temperature in the particulate pack may be maintained at an approximate formation temperature between about 200° F. and about 600° F., which approximately corresponds to the temperature of the deionized water first entering the system. A flow rate of simulated formation fluid may be maintained at approximately 1 milliliter per minute during the test.

The flow test may be maintained for between about 10 to about 200 days, and in an embodiment, for at least about 20 days. After this time, the particulate pack may be disassembled in order to test the mechanical properties of individual particles, as discussed in more detail below. For example, surface and compositional analysis may be made after disassembly to determine what types of materials are being formed under the simulated formation conditions. A permeability test may also be performed at this time. In this test, the permeability of the particulate packs may be measured at room temperature prior disassembly of the particulate pack. The measured permeability of the pack may then be compared with an initial permeability measurement made of the pack at room temperature before the pack is placed in the testing apparatus. Comparing the initial permeability measurement with the permeability measurement obtained after the pack is subjected to the test conditions may allow for a retained permeability to be calculated.

The stress/temperature-promoted diagenesis test method may involve the testing of the particulate pack under static flow conditions at approximate formation pressures and temperatures. In this method, a pack of particulates may be loaded in a test cell and filled with a salt solution. The test cell may be loaded from between about 0.5 pounds per square foot ($lb/ft^2$) of particulates to about 3.0 $lb/ft^2$ of particulates. In an embodiment, an approximately 2% KCl solution may be used as the fluid medium. Formation wafers, either manufactured from formation core material or from rock outcrop material, may be placed above and below the particulate pack in the test column. The system may then be shut in and placed under simulated formation pressure and heated to approximate formation temperatures. In an embodiment of this method, the temperature may be maintained at between about 100° F. and about 550° F. In another embodiment, the temperature may be maintained at between about 100° F. and about 350° F. The pressure may be maintained at between about 2,000 psi and about 10,000 psi. In another embodiment, the pressure may be maintained at between about 5,000 psi and about 8,000 psi. In an embodiment, the test may be conducted for between about 1 to about 50 weeks, and in another embodiment, the test may be conducted for at least about 4 weeks (about 28 days).

Upon completion of the stress/temperature-promoted diagenesis test, the test cell may be disassembled and the particulate pack removed for testing. As with the flow test method, additional tests may also be performed at this time. For example, surface and compositional analysis may be made after disassembly to determine what types of materials are being formed under the simulated formation conditions. Alternatively, the resulting interstitial fluid may be analyzed to determine the relative solubility of the particulates under formation conditions.

Changes in the mechanical properties of the particulates obtained from either the stress/temperature-promoted diagenesis test or the temperature-promoted diagenesis test may be determined using a single-grain crush-strength analysis. The analysis may utilize a Weibull statistical analysis procedure based on a plurality of particulate crush samples. The crush test may be based on a uni-axial compressive point loading of a particle. Under a compressive loading in the uni-axial direction, a spherical particle may be under tension in directions perpendicular to the loading with a tensile stress, σ, calculated by $$\sigma = \frac{2.8F}{\pi d^2}$$

where d is the diameter of each particle and F is the load at failure.

A Weibull analysis may include a statistically significant number of crush samples, which may range from about 10 to about 50 individual crush samples, or from about 20 to about 40 individual crush samples. In an embodiment, a sample size of between about 25 and about 30 individual crush samples of particulates may be used in the analysis. All of the strength data points may then be sorted from low to high as $\sigma_1 < \sigma_2 < \sigma_3 < \ldots < \sigma_N$, where N represents the total number of samples. A probability of failure may be calculated from the equation:

$$P_f = \left(\frac{\# - 0.5}{N}\right)$$

where, as before, N is the total number of samples, for example about 30 samples, and # is the index number for the sorted strength values (e.g., 1 through N). A linear plot may be obtained by plotting $$\ln\left(\ln\left(\frac{1}{1-P_f}\right)\right) vs \ln(\sigma)$$

A Weibull distribution may be found by linear fitting and generating an equation:

$$\ln\left(\ln\left(\frac{1}{1-P_f}\right)\right) = m\ln\left(\frac{\sigma}{\sigma_0}\right)$$

where m is the Weibull modulus and $\sigma_0$ is the characteristic strength. The strength will tend to increase along with the reliability of the strength calculation when the $\sigma_0$ and m values increase. The characteristic strength changes in the particulates may then be determined. By comparing the characteristic strength of the particulates prior to exposure to the simulated formation fluid with the characteristic strength of the particulates after exposure to the simulated formation fluid, a retained strength value may be calculated from the equation:

$$\sigma_{0retained} = \left(\frac{\sigma_{0exposed}}{\sigma_{0unexposed}}\right)$$

where, $\sigma_{0\ exposed}$ is the characteristic strength of the particles after exposure to the simulated formation fluid, and $\sigma_{0\ unexposed}$ is the characteristic strength of the particles prior to exposure. Similarly, a retained permeability may be calculated by dividing the permeability measured at the end of the temperature-promoted diagenesis test with the permeability measured at the beginning.

In an embodiment, a single set of test conditions may be utilized for comparison of different sets of sets of particles comprising diffusion barriers and/or filler materials. The retained strength value is defined to be measured by the stress/temperature-promoted diagenesis test. In this method, a pack of particulates is loaded in a test column and filled with a salt solution comprising an approximately 2% KCl solution. The test cell is loaded with about 2 lb/ft² of particulates. Formation wafers are placed above and below the particulates in the test cell. The system is then shut in and placed under a pressure that is approximately equal to the pressure expected in the formation in which the particulates are expected to be placed. The temperature may be maintained at a temperature that is approximately equal to the formation temperature where the particulates are expected to be placed. For example, the system may be placed under simulated formation pressure of about 9000 psi and temperature of about 250° F. These conditions are then maintained for about 28 days.

Upon completion of the stress/temperature-promoted diagenesis test, the test cell is disassembled and the particulate matrix removed for testing. Changes in the mechanical properties of the particulates are obtained using particulates tested using the stress/temperature-promoted diagenesis test. The analysis utilizes a Weibull statistical analysis procedure based on a plurality of particulate crush samples, as discussed above. A single analysis includes a statistically significant number of samples, which may be between about 20 and about 40 samples, e.g., approximately 30 crushed samples of individual particles. However, in some instances, the sample size may vary such that the actual number of samples is smaller or larger in order to obtain a statistically significant number of samples. The characteristic strength changes in the particulates may then be determined. By comparing the characteristic strength of the particulates prior to exposure to the simulated formation fluid with the characteristic strength of the particulates after exposure to the simulated formation fluid, a retained strength value is calculated from the equation:

$$\sigma_{0retained} = \left(\frac{\sigma_{0exposed}}{\sigma_{0unexposed}}\right)$$

where, $\sigma_{0\ exposed}$ is the characteristic strength of the particles after exposure to the simulated formation fluid, and $\sigma_{0\ unexposed}$ is the characteristic strength of the particles prior to exposure.

Similarly, the retained permeability value of the particulate pack is defined to be measured by the temperature-promoted diagenesis test. In the temperature-promoted diagenesis test procedure, an initial permeability measurement is made of a particulate pack while the particulate pack is at room temperature. Deionized water is then heated to a test temperature of approximately 500° F. by passing it through a heat exchanger coil. Lower test temperatures may also be used depending on the specific particulate material and coating used. For example, one of ordinary skill in the art may determine that a lower test temperature is required in order to avoid thermal decomposition of the particulates, the diffusion barrier, or the filler material. Simulated formation fluid is formed by passing the deionized water through multiple packs of crushed formation material arranged in series. The number of formation packs required for the test may vary such that the simulated formation fluid leaving the last pack is in equilibrium with the crushed formation material at the flow rate used during the test of approximately 1 milliliter per minute. The typical number of formation packs is generally between about 2 and about 5. Crushed formation material is screened and an approximately 8/35 mesh fraction is used in the formation packs. The formation material is obtained by crushing a core withdrawn from a specific well during drilling or from dill cuttings obtained while a well is being drilled through a zone of interest.

The simulated formation fluid is then directed to a column containing a particulate pack. The temperature in the particulate pack is maintained at a temperature of about 500° F. A lower test temperature may be used depending on the specific particulate material and coating material used. For example, one of ordinary skill in the art may determine that a lower test temperature is required in order to avoid thermal decomposition of the particulates, the diffusion barrier, or the filler. A flow rate of simulated formation fluid is maintained at approximately 1 milliliter per minute during the test. The flow test is maintained for about 30 days. After this time, permeability of the particulate pack is measured prior to disassembly and after the particulate pack has been allowed to cool to room temperature, allowing for a retained permeability to be calculated from the equation:

$$Permeability_{retained} = \left( \frac{Permeability_{exposed}}{Permeability_{unexposed}} \right)$$

where, $Permeability_{exposed}$ is the permeability of the particles after exposure to the simulated formation fluid, and $Permeability_{unexposed}$ is Permeability the permeability of the particles prior to exposure.

Particulates prepared and tested according to the methods of the current invention using the characteristic conditions of the embodiment may exhibit a retained strength value of greater than about 20%. Alternatively, the particulates may exhibit a retained strength value of greater than about 60%. In still another embodiment, the particulates may exhibit a retained strength value of greater than about 80%. In yet another embodiment, the particulates may exhibit a retained strength value of greater than about 90%. In an embodiment, the particulates used to form a pack may be characterized by a retained permeability value of at least about 40%. In another embodiment, the particulates may be characterized by a retained permeability of at least about 60%. In still another embodiment, the particulates may be characterized by a retained permeability of at least about 80%. In some embodiments, the retained permeability may be at least about 99%.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A composition comprising:
    a carrier fluid;
    a plurality of particulates, at least some of the particulates having a coating applied thereto that at least partially covers the particulates and impedes the intrusion of water into the particulates; and
    a silica scale control additive in the carrier fluid at a concentration between about 1 and 1000 parts per million by weight of the carrier fluid, wherein the silica scale control additive is capable of suppressing silica scale build-up proximate the plurality of particulates;
        wherein the coating is less than about 10 micrometers thick and comprises at least one hydrophobic substance selected from the group consisting of: a reaction product of a compound having a reactive silyl group, a silicon oxide anchor layer upon which a chloroalkylsilane is deposited, a hybrid organo-silicon oxide anchor layer upon which a chloroalkylsilane is deposited, a silicone, a siloxane, a diffusion barrier comprising a trimethylsilyl functional group, an organosiloxane, an organosilane, a fluoro-organosiloxane, a fluoro-organosilane, a polysiloxane, an organomodified polysiloxane, a di-betaine polysiloxane, a di-quaternary polysiloxane, a polymer of a fluoroalkyl-group containing silane compound, a dimer of a fluoroalkyl-group containing silane compound, a trimer of a fluoroalkyl-group containing silane compound, a polyamide, a silyl-modified polyamide, and copolymerized polyvinylidene chloride.

2. The composition of claim 1, wherein the silica scale control additive comprises at least one substance selected from the group consisting of: a polyaminoamide dendrimer, a polyethyleneimine, a carboxymethylinulin, a polyacrylate, a polyallylamine, a copolymer of polyacrylamide, a polyallyldimethylammonium chloride, and any combination thereof.

3. The composition of claim 1, wherein the plurality of particulates comprise at least one substance selected from the group consisting of a sand, a sintered bauxite, a silica alumina, a glass bead, a bauxite, a fumed silica, a ceramic material, a glass material, a polymer material, a polytetrafluoroethylene material, a degradable particulate, and any combination thereof.

4. The composition of claim 1, wherein at least some of the plurality of particulates are disposed in a particulate pack in a subterranean formation, the particulate pack having a retained permeability of about 40% or more as determined using a temperature-promoted diagenesis test using formation conditions expected for the subterranean formation.

5. The composition of claim 1 wherein the carrier fluid has a pH of greater than or equal to about 4.0 and less than or equal to about 8.0.

6. The composition of claim 1 wherein the carrier fluid is selected from the group consisting of an aqueous fluid, a hydrocarbon fluid, and an emulsion.

\* \* \* \* \*